(12) United States Patent
Buhlmann et al.

(10) Patent No.: US 9,452,282 B2
(45) Date of Patent: Sep. 27, 2016

(54) ELECTRODE SET AND STIMULATING DEVICE

(75) Inventors: Felix Buhlmann, Lausanne (CH); Klaus Schonenberger, Mex (CH); Pierre-Yves Lampo, Morrens (CH)

(73) Assignee: DJO Global Switzerland Sarl, Ecublens (FR)

( * ) Notice: Subject to any disclaimer, the term of this patent is extended or adjusted under 35 U.S.C. 154(b) by 1219 days.

(21) Appl. No.: 12/441,167

(22) PCT Filed: Sep. 13, 2007

(86) PCT No.: PCT/IB2007/053701
§ 371 (c)(1),
(2), (4) Date: Apr. 7, 2010

(87) PCT Pub. No.: WO2008/032282
PCT Pub. Date: Mar. 20, 2008

(65) Prior Publication Data
US 2010/0191316 A1    Jul. 29, 2010

(30) Foreign Application Priority Data

Sep. 13, 2006  (EP) ..................... 06120599
Feb. 8, 2007   (EP) ..................... 07101987
Mar. 30, 2007  (EP) ..................... 07105400
Jun. 29, 2007  (EP) ..................... 07111474

(51) Int. Cl.
*A61N 1/04*   (2006.01)
*A61N 1/05*   (2006.01)

(52) U.S. Cl.
CPC ........... *A61N 1/0551* (2013.01); *A61N 1/0452* (2013.01); *A61N 1/0456* (2013.01); *A61N 1/0476* (2013.01); *A61N 1/0492* (2013.01); *A61N 1/0412* (2013.01); *A61N 1/0428* (2013.01)

(58) Field of Classification Search
CPC ............. A61N 1/0452; A61N 1/0551; A61N 1/0476; A61N 1/0492; A61N 1/0456; A61N 1/0412; A61N 1/0428
USPC ........................................................ 607/115
See application file for complete search history.

(56) References Cited

U.S. PATENT DOCUMENTS

| | | | | |
|---|---|---|---|---|
| 4,164,226 A | * | 8/1979 | Tapper | A61N 1/0432 607/75 |
| 4,474,570 A | * | 10/1984 | Ariura | A61N 1/044 604/20 |
| 6,009,345 A | * | 12/1999 | Hofmann | A61N 1/303 435/173.6 |

FOREIGN PATENT DOCUMENTS

| | | |
|---|---|---|
| WO | WO-99/22809 | 5/1999 |
| WO | WO-99/22810 | 5/1999 |

*Primary Examiner* — Alyssa M Alter
(74) *Attorney, Agent, or Firm* — Knobbe Martens Olson & Bear LLP

(57) ABSTRACT

The electrode set for a stimulation device, such as a TENS or EMS stimulation device comprises at least a plurality of neighboring electrically active zones close to each other said active zones forming a succession of poles of alternating polarity or being grouped to form groups of poles of alternating polarity, wherein at least one of said active zone or group of zones has a lateral size ($D_2$) of approximately 1 mm to 40 mm, wherein at least one of spacing ($D_1$) between neighboring active zones or groups of zones is approximately of 1 mm to 40 mm, and said set further comprises contacting means connected to said active zones or groups of active zones.

24 Claims, 11 Drawing Sheets

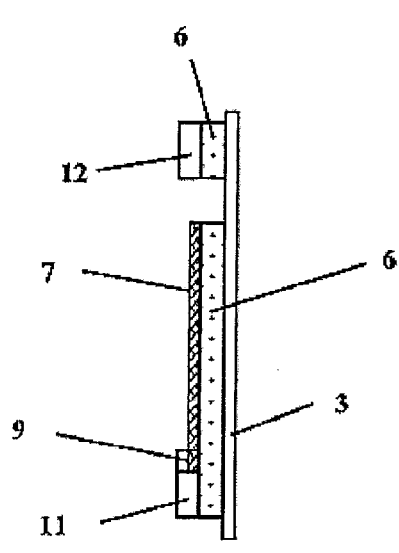
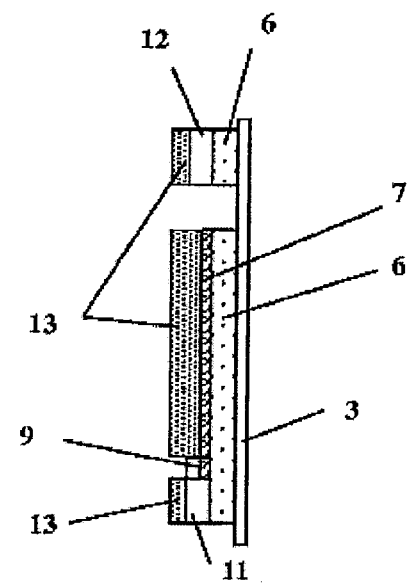
Figure 3A              Figure 3B
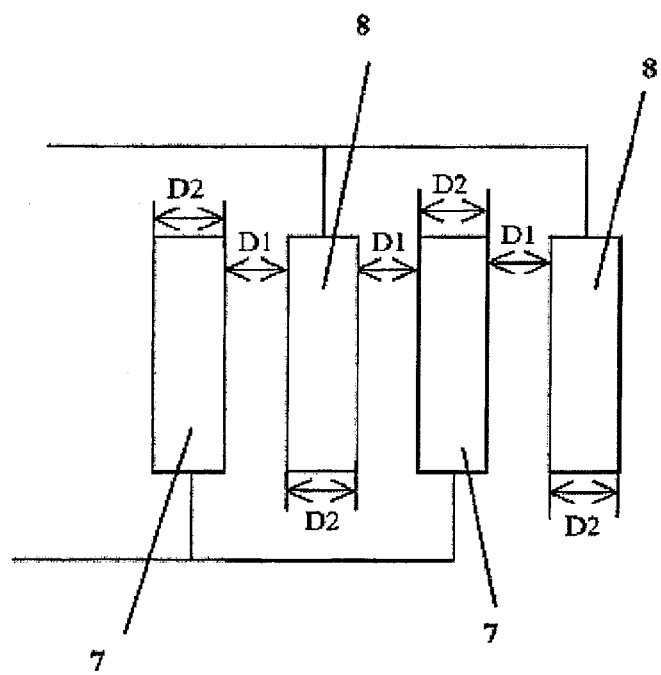
Figure 4

ELECTRODE SET AND STIMULATING DEVICE

RELATED APPLICATIONS

This application claims priority to EP Patent Application No 06120599.3 filed Sep. 13, 2006, EP Patent Application No 07101987.1 filed Feb. 8, 2007, EP Patent Application No 07105400.1 filed Mar. 30, 2007 and EP Patent Application No 07111474.8 filed Jun. 29, 2007 all incorporated herein by reference in their entirety.

FIELD OF THE INVENTION

The present invention concerns a stimulation electrode set, for example an electrode set for TENS or EMS stimulation, and a stimulating device comprising such electrode sets.

The present invention also concerns a method for optimizing parameters of electrode sets according to the present invention and treatments using an electrode set according to the present invention.

BACKGROUND OF THE INVENTION

Electrodes and stimulating devices are known as such in the prior art for different treatments of the human body. An example of an electrotherapy transducer is given in EP 0 638 330 which comprises a sheet of support material with a number of electrodes arranged in a matrix-like structure, adjacent electrodes receiving electric signals of opposite polarity. In a second embodiment, the structure of the electrodes is comb-shaped with electrodes being arranged alternately and equally spaced in relation to one another. This electrotherapy device is said to be used for the treatment of cellulitis or for the treatment of muscles but not much more information is given on the structure of the device, or on the electrical signals used during a treatment.

In the field of electrical stimulation, two stimulation principles are known: transcutaneous electrical nerve stimulation (TENS) on the one hand, and electrical muscular-type stimulation (EMS) on the other hand. TENS stimulation devices are used for the treatment of pain whereas EMS stimulation devices are used for physical therapy and body building, for example for correcting muscle atrophy, stimulating muscle growth and increasing range of motion.

Devices that apply such TENS and/or EMS stimulations to the body of a user are known per se in the art.

As an illustrative example, application EP 1 095 670 which is incorporated by reference in the present application, describes a neuromuscular electrical stimulator using stimulation electrodes and an electrical impulse generator. This device is mainly used for EMS stimulation and it comprises at least two electrodes spaced apart and placed on a part to be treated of the human body. A stimulator is connected to the electrodes through connection wires and it sends the desired electrical signals to the electrodes in order to stimulate the muscles.

With specific respect to TENS, this type of treatment has been extensively described in the art. As a reference, one may cite the publication "Electrotherapy 11$^{th}$ Edition Evidence-based practice", October 2001 by Sheila Kitchen, MSc, PhD, DipTP, MSCP, Head, Division of Physiotherapy, King's College, London.

Chapter 17 of this publication relates to "Transcutaneous Electrical Nerve Stimulation (TENS)" by Mark Johnson, incorporated by reference in the present application, and reference is made to this Chapter for the theory and explanations relating to TENS treatments. As can be understood from this publication, TENS is "the most frequently used electrotherapy for pain relief, and reference is made to this publication for the theory explaining and demonstrating the effects of TENS stimulation and also the theory of "The Pain Gate".

According to the above-mentioned article of Mark Johnson (see FIG. 17.2) under normal physiological circumstances, the brain generated pain sensations by processing incoming noxious information arising from stimuli such as tissue damage. The noxious information reaches the brain by passing through a metaphorical "pain gate" located in the lower levels of the central nervous system. The pain gate may be closed by activation of various sensory afferents, i.e. through rubbing the skin which generates activity in large diameter Aβ afferents which inhibits the onward transmission of noxious information.

It is therefore an aim of conventional TENS to selectively activate Aβ fibers using electrical currents to provide segmental analgesia.

Another way to close the pain gate is to activate pain-inhibitory pathways which originate in the brain and descend to the spinal cord through the brainstem. Accordingly, an aim of AL TENS (Acupuncture-like TENS) is to activate small diameter peripheral fibres to activate the descending pain-inhibitory pathways. This stimulation however provokes a muscle contraction.

Another way to produce peripheral blockade of nociceptive afferent activity and segmental and extrasegmental analgesia is to use Intense TENS to activate small diameter Aδ cutaneous afferents by delivering said TENS stimulation over peripheral nerves arising from the site of pain at an intensity which is just tolerable to the patient (using high-frequency and high-intensity currents).

During classical and Intense TENS stimulation programs, it is important to stimulate only the sensitive nerve cells end not the motor nerves, which will induce a tetanic muscle contraction which can be painful, an effect contrary to the one sought.

One of the problems to which the user of stimulators is confronted is the positioning of the electrodes on the body in view of the desired treatment and also the sizes of the electrodes used for a given treatment.

Another example of a stimulation device is given in US 2002/0077688. This publication relates to a body garment which is used in combination with an electrical muscle and/or nerve stimulation device. In this publication, the body garment is specifically structured to position the electrode pads at predetermined positions on the body corresponding with different muscle or nerve groups and it is connected to a TENS unit controller or an EMS unit controller for the desired stimulation. As taught in this document, the garment may cover the entire body of the user or only a part of said body.

Another publication of the prior art relating to TENS stimulation is WO 2005/002668. In this publication, the problem identified to be solved is adaptation. This occurs when although the amplitude and frequency of the stimulation are subjected to changes, the polarity of the electrodes is not changed so that the nerve cells which are subjected to the same stimulation adapt to said stimulation. Accordingly, an idea of this publication is to provide an electrode system with at least two poles which are separated by an insulating material to prevent a short-circuit between the poles and allowing the poles to be provided with electrical fields by stepwise alternating the negative current from one pole to the next pole. This causes two different areas to be stepwise treated by the electrode system. In one embodiment, the system includes four poles such that the electrical field may move between the poles. Since the action potential is initiated mainly below the negative pole, the treatment seems to wander over the surface covered by the electrode.

Another publication WO 2005/075018 relates to a device for neuromuscular stimulation. In this publication, the stimulation apparatus comprises a nerve stimulation array electrode comprising a substrate for application to the skin of a user bearing an array of electrodes arranged to be brought into electrical contact with the skin of the user, input contacts and user operable switch means for making or breaking the electrical contact between said input contacts and any selected one or ones of said electrodes allowing the user to freely form any group of electrodes. In addition, the apparatus comprises a separate common ground or counter electrode which will not generally need to be in the form of an array. This design allows in particular the practitioner or the patient to find which electrodes in the array contribute most effectively to producing the desired stimulation effect and he can thus form a specific group accordingly.

Another publication related to TENS treatment is WO 2005/065770. In this publication, the device comprises a current generating device configured to generate first and second types of electrical TENS currents. The construction allows a specific localized superficial blockade by an appropriate targeting of the intra epithelial and dermal nerves. More specifically, the device further comprises an array of electrodes to be placed around an injection location on the skin of a patient, said array being electrically coupled to the current generating device. The electrodes comprise a first and a second group, the first group being configured to be placed closer than the second group to the injection location on the skin of the patient. Typical sizes of electrodes are approximately 0.8 mm of width or diameter, an area of approximately 0.5 $mm^2$ and the distance between the electrode is no more than 2 mm. Preferably, in this publication, the distance is less than 1 mm or even less than 0.5 mm. The current applying device is configured to apply the first type of TENS current to the first group of electrodes and apply the second type of TENS current to the second group of electrodes. By activating electrodes in pairs around the injection location, a ring of discharge pathways though the patient's skin may be sequentially created thereby providing a good coverage of the sensory nerves in the area. The voltage signals applied to the inner electrodes in particular may depolarize the nerves within the skin to thereby suppress pain sensitivity.

Other examples of TENS treatment devices and method are described in publications WO 93/22966, U.S. Pat. No. 5,785,040, U.S. Pat. No. 6,301,500 and US 2002/0055762. The content of all publications cited above are incorporated by reference in the present application.

Another field using electrodes applied to a patient is iontophoresis. This technique is generally defined as a non-invasive method of propelling high concentrations of a charged substance, normally medication or bioactive-agents, transdermally by repulsive electromotive force using a small electrical charge applied to an iontophoretic chamber containing a similarly charged active agent and its vehicle. Although using electrodes as well, this method and the devices used are in fact very different from methods and devices used in the field of TENS or EMS stimulation, in particular because of the effect sought and principle of functioning of the respective devices.

Such iontophoretic devices are used for example to inhibit perspiration from human hands, feet or underarms and also for the treatment of varied dermato logic and cosmetic problems.

Use of an iontophoretic device is for example described in U.S. Pat. No. 4,164,226. In this patent, the device comprises intermingled negative and positive electrodes (forming an array) all having porous material to carry out the iontophoretic effect.

WO 93/00959 shows another device and method to deliver topical drugs to an area of tissue to be treated by iontophoresis. In this publication the electrodes are made by two electrode patterns each including a set of substantially parallel electrodes being arranged in an alternating arrangement.

Other devices described in US 2002/055703 and U.S. Pat. No. 5,968,006 are used both for iontophoresis and electroporation. In both publications, an electrode structure has the shape of interdigitated comb-like electrode pairs. However, in such field, the use of electrodes is combined with a porous material or a chamber to carry out the iontophoretic effect and the electrical signal is not used to stimulate nerves or muscles as in a TENS or EMS system.

SUMMARY OF THE INVENTION

According to the principle of the invention, for a TENS stimulation, one uses electrodes of small surface, close to each other. Indeed, in this case, the density of current generated remains constant in a small depth of skin under the electrode and it diminishes quickly by current dispersion, such that the effective stimulation remains close to the surface. Conversely, in muscular stimulation programs, one wants to go deeper in order to affect the muscles. To this effect, one rather uses electrodes with a larger surface such that the constant current density under the electrode penetrates deeper in the skin before its dispersion.

Similarly, depending on the type of stimulation desired (TENS or EMS), the relative position of the electrodes has an importance. For a TENS stimulation, the two electrodes should be closer to each other whereas for EMS stimulation, the two electrodes should be spaced apart. Moreover, the position of electrodes cannot be chosen arbitrarily in that if they are too close, the stimulation may not penetrate enough in the body of the user to achieve the desired stimulation.

Also, as can be understood from previous designs, the proper positioning of at least two separate electrodes might be a problem for a user.

It is therefore an aim of the present invention is to improve the known systems.

More particularly, an aim of the invention is to provide an electrode structure that is more efficient for TENS stimulation and easy to use.

Another aim of the present invention is to provide a system that is capable of carrying out TENS or EMS stimulation.

A further aim of the present invention is to provide a system able to prioritize the stimulation of either sensitive or motor nerves as desired.

A further aim of the present invention is to propose a method for optimizing parameters of the electrode system in order to obtain a more efficient device than previously known.

A further aim of the present invention is to propose a stimulation method that uses the features of the electrode set according to the present invention.

An idea of the present invention is to form an electrode set with active zones of reduced surface area which are close to each other rather than two electrodes of a larger surface area that are distant such as is presently done. In a more detailed manner, the present invention provides optimized sizes and dimensions for the active zones forming the electrode. In the present invention, the notion of electrode should be interpreted in a broad sense as meaning a zone which is able to apply an electrical potential directly or indirectly to the body of the user.

The set of electrodes is used with a stimulator that is connected to the active zones, for example through cables or other suitable equivalent transmission means.

In one embodiment, one forms an electrode set with active zones that are intermingled in which one may choose freely the polarity of the injected currents thus forming a set of electrodes with alternating poles.

These active zones can be mounted on an isolating support backing (for example a fabric or another equivalent means) and then placed directly on the part of the body to be stimulated. This backing may be oversized in order to improve adhesion of the set to the skin.

In a variant, one uses a gel layer placed between the active zones and the surface of the body. The gel layer can be a continuous layer defined according to the parameters disclosed below and in reference to FIG. 10A-15, or a gel layer placed only over the surface of the active zones or even a gel paste or another conductive fluid.

The stimulator may be able to activate all the active zones of the set, or only a determined group. Accordingly, one may choose either a determined group, that is at least two active zones of opposite polarity which are close to each other (for example neighboring) if one wishes to stimulate preferably the sensory fibers or at least two active zones far apart from each other if one wishes to obtain a muscle stimulation.

Several embodiments and variants of the invention will be illustrated in the following detailed description of the invention.

BRIEF DESCRIPTION OF THE DRAWINGS

The invention will be best understood by the description of several embodiments and of the corresponding drawings in which

FIG. 3A shows a lateral cut view of the set of FIG. 2;

FIG. 3B shows a lateral cut view of a variant of the set of FIG. 2;

FIG. 4 shows a partial view of the set of the first or second embodiments;

DETAILED DESCRIPTION

Figure 1:
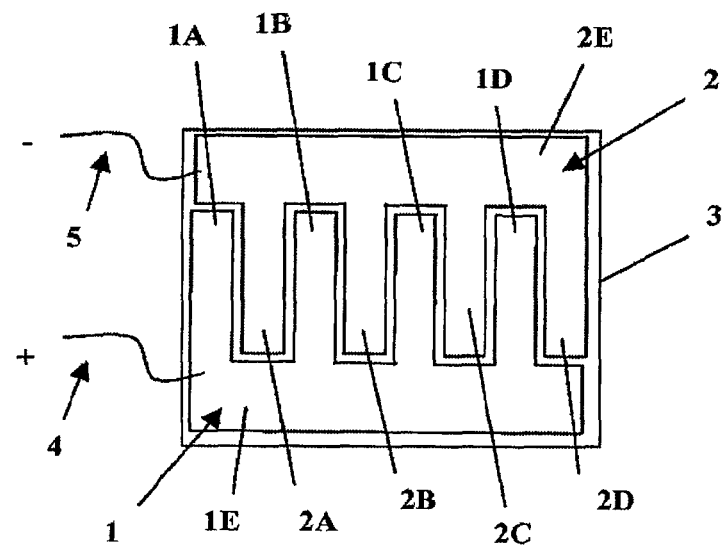
FIG. 1 shows a first embodiment of an electrode set viewed from below.

In the first embodiment of FIG. 1, one has represented a view from below (that is the side that will be in contact with the skin of the user) of an electrode set according to the invention. This set has two elements 1, 2 having a succession of intermingled active zones (having a rectangular shape in this FIG. 1A, 1B, 1C, 1D, 2A, 2B, 2C, 2D and a base 1E, 2E. The two elements 1, 2 are mounted on a first non-conductive layer 3 (for example a flexible fabric layer) and are connected each to contacting means 4, 5 for example wires for connection to a stimulator (not shown). In one embodiment, the wires 4, 5 are connected to the respective bases 1E, 2E. In the representation of FIG. 1, the active zones 1A-1D, 2A-2D have alternating polarities.

In some embodiments, the set represented comprises a lateral screen made of a non-conductive material and placed on the bases 1E, 2E of the set so that only the active zones 1A-1D, 2A-2D are in contact with the skin of the user.

It is of course understood that the screen is optional and that in other configurations, the set can be provided without such screen.

In FIG. 1, no gel has been represented but a gel layer may be provided at least over the active zones 1A-1D, 2A-2D. In some embodiments, a single gel layer covers all the active zones and the screen if present. In a variant, the gel layer is only present on the active zones.

Figure 2:
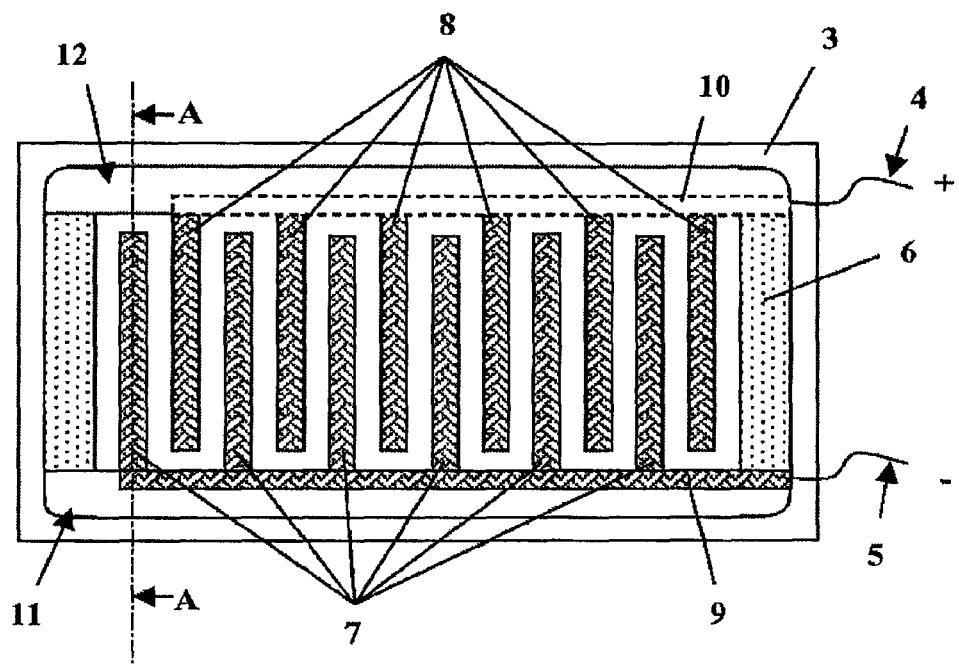
FIG. 2 shows a second embodiment of an electrode set viewed from below.

In FIG. 2, another embodiment is illustrated.

In this embodiment, a first non-conductive layer 3 (for example a fabric) is prepared. On this non-conductive layer 3, a layer of moderate conductive carbon 6 is placed, said layer 6 being cut to form the active zones 7 and 8. Over this layer 6, in order to effectively form the active zones, a printing of conductive ink (for example a silver-based ink or paint) is carried out on each active zone 7, 8. In addition, in order to connect the active zones 7, 8 to the wires 4, 5, a strip 9, 10 of conductive ink is also applied on both sides of the carbon layer. Finally, insulating layers 11, 12 (such as a screen) are applied on both sides of the carbon layer 6. The connection of the wires 4, 5 to the strips 9, 10 are for example made by glueing the end of the wires to the strips. Of course, other equivalent procedures are possible such as snap connectors. In the representation of FIG. 2, the side of the wires which is connected to the set is over the strips 9, 10 and underneath the insulating layers 11, 12.

In FIG. 2, the layer 11 is represented partially removed to show the strip 9, connecting the active zones to the wire 5, whereas the layer 12 is not removed in the illustration, hence the strip 10 which is underneath the layer 12 is represented in dashed line.

In some embodiments, a gel layer is added on the active zones 7, 8 to improve the conductivity and also on the insulating layers 11, 12. The gel layer could be a continuous layer or could be made of gel strips added mainly on the active zones.

As one will readily understand, the configuration illustrated in FIG. 2 is only one specific non-limitative realization and equivalent variants can be considered.

These variants will be described hereunder by identifying the successive layers forming the set according to the present invention.

The first layer can be a backing layer (non conductive layer, for example made of PVC or PP or a fabric) on which a conductive layer (for example of carbon) is placed. The contacting means (for example wires) may be placed between the backing layer and the conductive layer, or on the other side of the conductive layer with respect to the backing layer. In this variant, the conductive layer is cut to the desired shape thus directly forming the active zones. A conductive ink (for example silver based) may be deposited on the active zone cut into the conductive layer.

In this embodiment with a conductive layer, a screen non-conductive layer can be added to cover the parts of the conductive layer that should not contact the body of the user and also the wires if they are on the other side of the conductive layer with respect to the backing layer.

In another embodiment, the backing layer is made of a non-conductive layer (PVC, PP for example or a fabric) or of a non-conductive or low-conductive carbon layer and the active zones are made directly by the deposition of conductive ink on said backing layer or carbon (which does not have to be cut). In this embodiment, the contacting means (i.e. wires) can be placed over the conductive ink or between the ink and the non-conductive layer for electrical connection. If the wires are placed over the conductive ink (that is on the side of the body of the user), then a non-conductive screen layer can applied for covering the contact zone between the wires and the active zones in the manner taught in FIG. 2.

In FIG. 3A, a cut view along axis A-A of FIG. 2 is illustrated. The set is made of a first non-conductive layer of fabric 3 and a conductive layer 6 (for example carbon) on which the active zones 7, 8 are made with conductive ink. Optionally, as indicated above and represented in FIGS. 3A and 3B, the set may further comprise an insulating layer such as a screen 11, 12 and a gel layer 13 (represented in FIG. 3B).

The conductive layer is also optional and the active zones may be placed directly on the first non-conductive layer.

As indicated above, the conductive ink deposition is optional and in a simple configuration, one can use only a carbon conductive layer which has be cut to form the desired active zones shapes with contacting means such as wires connected to either side of the carbon layer.

Size parameters are illustrated in FIG. 4 which shows a schematical partial view of a set according to FIG. 1 or 2. In this example, the active zones are referenced 7 and 8 as in FIG. 2 but the principle explained in the following related to the sized and distances apply to all embodiments of electrode sets of the present invention.

In some embodiments, sizes for the lateral dimensions ($D_2$) of the active zones 7, 8 are from 1 mm to 40 mm and for the spacing ($D_1$) between active zones 7, 8 are from 1 mm to 40 mm.

In one embodiment, $D_1$ and $D_2$ are at least 2 mm.

In another embodiment $D_1$ and $D_2$ are about 5.5 mm.

In a further embodiment, $D_1$ and $D_2$ are about 3 mm.

In the embodiment of FIGS. 1 and 2, the set has a longitudinal size of about 130 mm and a lateral size of about 60 mm.

Of course, all these dimensions may be adapted depending on the configuration of the set chosen in among the variants described herein and also, in a given set of electrodes, the values of $D_1$ and $D_2$ may be varied so that the electrodes and the spacings may have different sizes.

Experimentally, it has been shown that these sizes were particularly advantageous for applying a TENS stimulation. Indeed, one has noticed that with the electrode set construction according to the invention, the thresholds of TENS or EMS stimulation (i.e. sensory vs. muscular) were well differentiated, whereas with a classical construction such as with large electrodes which are spaced apart, these thresholds were much closer and much more difficult to differentiate.

In the present specification the TENS threshold is understood as meaning the minimum current required to effectively reach and stimulate sensory fibers/nerves and the MOTOR threshold is the amount of current required to reach and stimulate the muscle fibers/nerves.

This differentiation effect is demonstrated in the following Tables 1.1-1.3, 2.1-2.3 and 3.1-3.3, in which the measurements provided show that with the electrode set according to the present invention, one obtains a ratio between the thresholds of TENS and MOTOR stimulation of up to 10 for small and close to each other active zones and a ratio of 1 for larger active zones which are distant.

With a well differentiated threshold, it is thus possible to increase the TENS treatment dosage, without reaching an undesired MOTOR stimulation. Hence the treatment is improved and more effective.

These tables are examples of TENS thresholds, MOTOR (muscular) thresholds and the ratio of both thresholds for three different test patients (first patient tables 1.1 to 1.3, second patient tables 2.1 to 2.3 and third patient tables 3.1 to 3.3). The columns define the active zone spacing D1 in mm, the lines define the active zone lateral dimension D2 in mm, and the values indicated in the tables are the current threshold in mA for TENS stimulation (Tables 1.1, 2.1, 3.1), current threshold for MOTOR stimulation (Tables 1.2, 2.2, 3.2) and the ratio EMS/MOTOR thresholds (Tables 1.3, 2.3, 3.3). The electrode width is 50 mm.

Typical signals used include a succession of a high frequency stimulation followed by a low frequency stimulation. For the tables indicated hereunder, the high frequency signal has the following parameters:

impulse width: 60 µs frequency: 120 Hz duration: 3 s

The low frequency signal has the following parameters:

impulse width: 60 µs frequency: 2 Hz duration: 3 s

The results given are typical of the values obtained when the electrodes are placed on different parts of the body of the patient.

As one can clearly see, the ratio increases if the electrodes size diminishes and also the distance between the electrodes diminishes. However, it has also been shown experimentally that if the values of D1 and D2 are too small, in particular less than 1 mm, the effect is not present anymore because the current does not reach the sensory fibers but goes directly from one pole to another (see for example the "no sensitive" effect mentioned further in the description and illustrated in FIG. 15).

TABLE 1.1

(current threshold TENS [mA])

| Spacing | \\ Size [mm] 1 | 2 | 3 | 5 | 7 | 10 | 15 | 25 | 40 |
|---|---|---|---|---|---|---|---|---|---|
| 1 | | | 5 | 5 | 5 | 4 | 5 | 6 | 6 |
| 2 | | | 5 | 4 | 4 | 4 | 5 | 5 | 5 |
| 3 | | | | | | | | | |
| 5 | | | 4 | 3 | 4 | 4 | 5 | 5 | 7 |
| 7 | | | | | | | | | |
| 10 | | | 4 | 3 | 4 | 4 | 5 | 6 | 7 |
| 15 | | | 4 | 3 | 4 | 4 | 5 | 6 | 7 |
| 25 | | | 4 | 3 | 4 | 3 | 5 | 6 | 7 |
| 40 | | | 4 | 3 | 4 | 3 | 5 | 5 | 7 |

TABLE 1.2

(current threshold MOTOR [mA])

| Spacing/Size [mm] | 1 | 2 | 3 | 5 | 7 | 10 | 15 | 25 | 40 |
|---|---|---|---|---|---|---|---|---|---|
| 1 | | | 48 | 43 | 30 | 23 | 25 | 26 | 24 |
| 2 | | | | | | | | | |
| 3 | | | | | | | | | |
| 5 | | | 44 | 35 | 22 | 19 | 25 | 23 | 23 |
| 7 | | | | | | | | | |
| 10 | | | 26 | 19 | 17 | 18 | 22 | 24 | 22 |
| 15 | | | 16 | 20 | 16 | 19 | 21 | 22 | 21 |
| 25 | | | 17 | 21 | 19 | 18 | 19 | 20 | 20 |
| 40 | | | 19 | 18 | 17 | 19 | 19 | 19 | 20 |

Grey cell: MOTOR threshold not reached

TABLE 1.3

(ratio thresholds MOTOR/TENS)

| Spacing | \\ Size [mm] 1 | 2 | 3 | 5 | 7 | 10 | 15 | 25 | 40 |
|---|---|---|---|---|---|---|---|---|---|
| 1 | | | 9.6 | 8.6 | 6.0 | 5.8 | 5.0 | 4.3 | 4.0 |
| 2 | | | | | | | | | |
| 3 | | | | | | | | | |
| 5 | | | 8.8 | 8.8 | 5.5 | 4.8 | 5.0 | 4.6 | 4.6 |
| 7 | | | | | | | | | |
| 10 | | | 6.5 | 6.3 | 4.3 | 4.5 | 4.4 | 4.8 | 3.1 |
| 15 | | | 4.0 | 6.7 | 4.0 | 4.8 | 4.2 | 3.7 | 3.0 |
| 25 | | | 4.3 | 7.0 | 4.8 | 6.0 | 3.8 | 3.3 | 2.9 |
| 40 | | | 4.8 | 6.0 | 4.3 | 6.3 | 3.8 | 3.8 | 2.9 |

TABLE 2.1

(current threshold TENS [mA])

| Spacing | \\ Size [mm] 1 | 2 | 3 | 5 | 7 | 10 | 15 | 25 | 40 |
|---|---|---|---|---|---|---|---|---|---|
| 1 | | | 6 | 8 | 9 | 11 | 11 | 13 | 16 |
| 2 | | | | | | | | | |
| 3 | | | | | | | | | |
| 5 | | | 7 | 9 | 9 | 10 | 10 | 12 | 15 |
| 7 | | | | | | | | | |
| 10 | | | 8 | 8 | 8 | 9 | 11 | 12 | 14 |
| 15 | | | 7 | 7 | 9 | 10 | 11 | 12 | 15 |
| 25 | | | 7 | 8 | 9 | 10 | 9 | 12 | 15 |
| 40 | | | 6 | 8 | 10 | 9 | 10 | 12 | 15 |

TABLE 2.2

(current threshold MOTOR [mA])

| Spacing/Size [mm] | 1 | 2 | 3 | 5 | 7 | 10 | 15 | 25 | 40 |
|---|---|---|---|---|---|---|---|---|---|
| 1 | | | 53 | 45 | 33 | 28 | 27 | 25 | 22 |
| 2 | | | | | | | | | |
| 3 | | | | | | | | | |
| 5 | | | 37 | 34 | 25 | 24 | 24 | 22 | 21 |
| 7 | | | | | | | | | |
| 10 | | | 28 | 24 | 22 | 21 | 24 | 21 | 21 |
| 15 | | | 24 | 20 | 19 | 19 | 22 | 19 | 21 |
| 25 | | | 19 | 17 | 17 | 19 | 20 | 18 | 21 |
| 40 | | | 17 | 16 | 16 | 18 | 19 | 17 | 20 |

Grey cell: MOTOR threshold not reached

TABLE 2.3

(ratio thresholds MOTOR/TENS)

| Spacing | \\ Size [mm] 1 | 2 | 3 | 5 | 7 | 10 | 15 | 25 | 40 |
|---|---|---|---|---|---|---|---|---|---|
| 1 | | | 8.7 | 5.6 | 3.7 | 2.5 | 2.5 | 1.9 | 1.4 |
| 2 | | | | | | | | | |
| 3 | | | | | | | | | |
| 5 | | | 5.3 | 3.8 | 2.8 | 2.4 | 2.4 | 1.8 | 1.4 |
| 7 | | | | | | | | | |
| 10 | | | 3.5 | 3.0 | 2.8 | 2.3 | 2.2 | 1.8 | 1.5 |
| 15 | | | 3.4 | 2.9 | 2.1 | 1.9 | 2.0 | 1.6 | 1.4 |
| 25 | | | 2.7 | 2.1 | 1.9 | 1.9 | 2.2 | 1.5 | 1.4 |
| 40 | | | 2.8 | 2.0 | 1.6 | 2.0 | 1.9 | 1.4 | 1.3 |

TABLE 3.1

(current threshold TENS [mA])

| Spacing | \\ Size [mm] 1 | 2 | 3 | 5 | 7 | 10 | 15 | 25 | 40 |
|---|---|---|---|---|---|---|---|---|---|
| 1 | | | 4 | 4 | 5 | 6 | 7 | 9 | 8 |
| 2 | | | | | | | | | |
| 3 | | | 4 | 3 | 5 | 6 | 8 | | |
| 5 | | | 4 | 5 | 5 | 6 | 8 | 9 | 9 |
| 7 | | | | | | | | | |
| 10 | | | 4 | 4 | 6 | 7 | 8 | 9 | 9 |
| 15 | | | 4 | 4 | 5 | 7 | 7 | 7 | 9 |
| 25 | | | 4 | 4 | 5 | 7 | 7 | 9 | 9 |
| 40 | | | 4 | 3 | 5 | 7 | 8 | 9 | 8 |

TABLE 3.2

(current threshold MOTOR [mA])

| Spacing/Size [mm] | 1 | 2 | 3 | 5 | 7 | 10 | 15 | 25 | 40 |
|---|---|---|---|---|---|---|---|---|---|
| 1 | | | | 28 | 34 | 22 | 23 | 18 | 16 |
| 2 | | | | | | | | | |
| 3 | | | | 26 | 33 | 23 | 21 | | |
| 5 | | | | 25 | 33 | 22 | 20 | 17 | 16 |
| 7 | | | | | | | | | |
| 10 | | | 29 | 24 | 25 | 19 | 17 | 15 | 16 |
| 15 | | | 23 | 20 | 21 | 17 | 17 | 15 | 16 |
| 25 | | | 16 | 16 | 16 | 15 | 16 | 15 | 15 |
| 40 | | | 15 | 14 | 14 | 14 | 15 | 15 | 15 |

Grey cells: MOTOR threshold not reached

TABLE 3.3

(ratio thresholds MOTOR/TENS)

| Spacing | 1 | 2 | 3 | 5 | 7 | 10 | 15 | 25 | 40 |
|---|---|---|---|---|---|---|---|---|---|
| 1 | | | 10.0 | 7.0 | 6.8 | 3.7 | 3.3 | 2.0 | 2.0 |
| 2 | | | | | | | | | |
| 3 | | | 9.5 | 8.7 | 6.6 | 3.8 | 2.6 | | |
| 5 | | | 8.3 | 5.0 | 6.6 | 3.7 | 2.5 | 1.9 | 1.8 |
| 7 | | | | | | | | | |
| 10 | | | 7.3 | 6.0 | 4.2 | 2.7 | 2.1 | 1.7 | 1.8 |
| 15 | | | 5.8 | 5.0 | 4.2 | 2.4 | 2.4 | 2.1 | 1.8 |
| 25 | | | 4.0 | 4.0 | 3.2 | 2.1 | 2.3 | 1.7 | 1.7 |
| 40 | | | 3.8 | 4.7 | 2.8 | 2.0 | 1.9 | 1.7 | 1.9 |

Hence, a TENS treatment using the set according to the invention is much more effective since the TENS and MOTOR thresholds are well separated.

Accordingly, the range of current values that can be selected for a TENS stimulation without reaching the MOTOR threshold is larger and the TENS treatment is more efficient because it can apply higher intensities which are more efficient.

An advantage of the invention is the following: to overcome adaptation, the user may for example increase the stimulation current without reaching the MOTOR threshold.

A second advantage is to avoid pain, when the user has muscle pain. Again, an unwanted muscle stimulation is avoided. Indeed, muscle twitches or tetanic contractions are undesired for daily living. The invention thus provides a better use of TENS stimulation for a longer period, which amounts to better pain relief.

A third advantage resides in the simplicity of the system: placing electrodes where it hurts, as opposed to placing multiple electrodes around a painful area as taught in the prior art. Since the delivered current will not penetrate the tissue deep enough to stimulate the muscle, thereby neither aggravating an injured muscle nor causing pain, the electrode set can be placed directly on the painful area.

Figure 5:
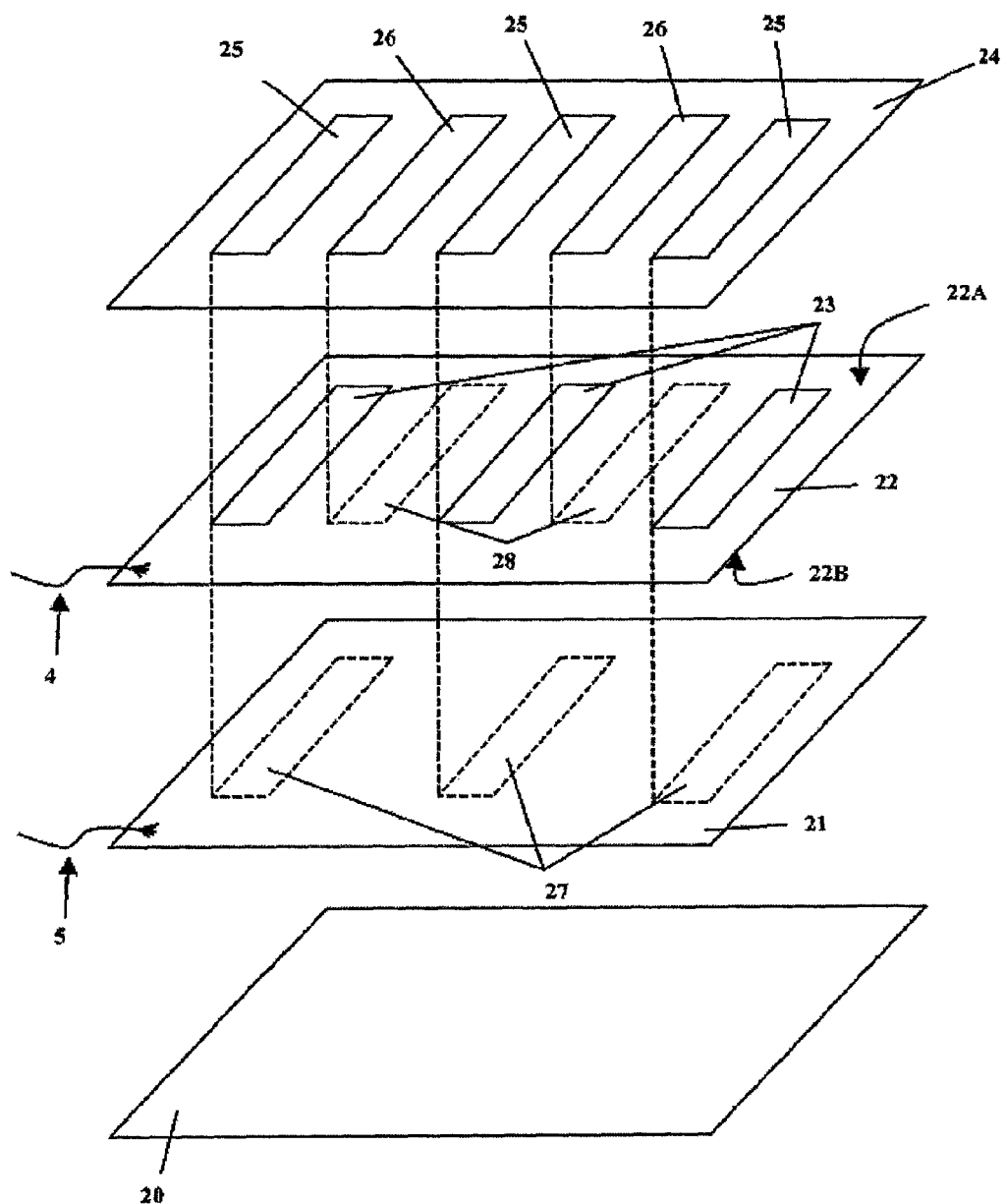
FIG. 5 shows another embodiment of the set of the invention.

FIG. 5 shows another embodiment of the invention. In this embodiment, the set of electrodes is made of several layers of different materials, some of the them comprising cut or punched out holes/openings to form the active zones.

This embodiment comprises a first non-conductive backing layer 20, similar to the backing layer 3 described above. Such backing can be a fabric backing and may be oversized to improve adhesion to the skin.

On this layer 20, a second conductive layer 21, for example, a carbon conductive layer (or another equivalent material) is placed, said layer 21 being connected to a wire 5.

Over this layer, a third layer 22 is placed, this layer 22 having a conductive side 22A, for example a carbon layer or another equivalent, connected to a wire 4 and a non-conductive side 22B for example a layer of PVC or PP or another equivalent material. The non conductive side 22B is on the side in contact with the conductive layer 21. This side of the layer 22 is rendered non-conductive for example by the application of a thin foil of non-conductive material. Other equivalent solutions are of course possible. This third layer 22 as a mask comprises openings 23 that allow contact with the layer 21, these contact zones being illustrated in dashed lines on layer 21.

Over this third layer, a fourth non-conductive layer (for example made of PVC or PP or another equivalent material) is provided as a top mask 24. This top mask also has two groups of openings 25, 26, the first group of openings 25 being aligned with the openings 23 of the third layer 22 as illustrated by the vertical dashed lines and the second group of openings which only allow contact with the third layer 22.

This construction allows the formation of an electrode set with neighboring active zones, according to principle of the present invention, through the openings made in the different layers.

For the sake of illustration, these active zones have been schematically represented in FIG. 5 with dashed lines and are referenced 27 and 28. The principles described above relating to the lateral sizes of the active zone (D2) and the distance between active zones (D1) apply correspondingly to this embodiment. In addition, FIG. 5 is an illustration of an embodiment where the number of active zones (and of openings) can be varied with respect to what is shown. There can be more or less active zones than represented and also an even or odd number of active zones.

A gel layer is added on the top mask 24, said gel being either a uniform layer deposited on the entire surface or a layer cut and/or deposited selectively only on the active zones.

The principle of the present invention may be used with other shapes of active zones, for example, circular, in which case the set could made of a number of concentrical circular active zones. In other variants, the active zone may have an oval shape or any other shape or conformation suitable for application to the body. Such other shapes and configuration are illustrated in FIGS. 6A to 6D by way of non-limiting examples with the distances $D_1$ and $D_2$.

Figure 6A:
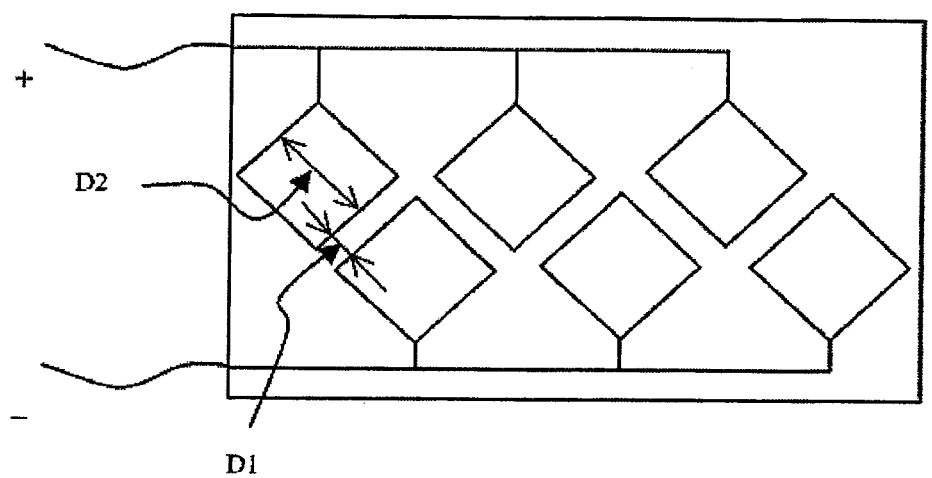
FIGS. 6A to 6D illustrate in a schematical way different shapes of active zones.
Figure 6B:
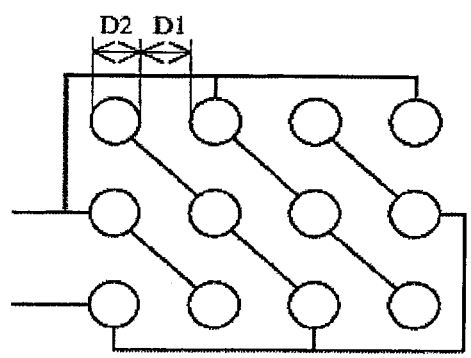
Figure 6C:
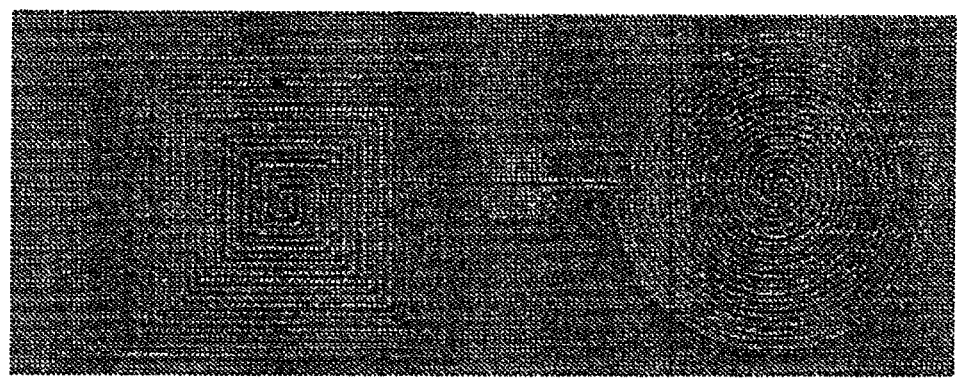
Figure 6D:
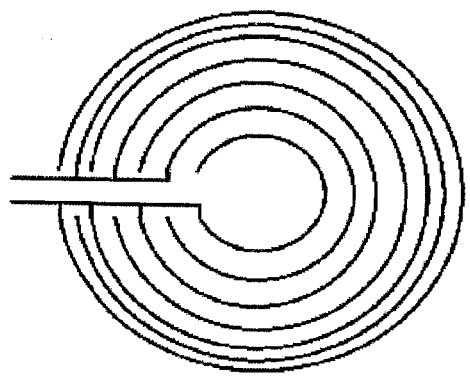

For example, FIG. 6A shows a checkerboard configuration of active zones; in FIG. 6B the active zones are circular and disposed in a matrix-like arrangement. FIGS. 6C and 6D illustrate schematically other configurations.

Figure 7A:
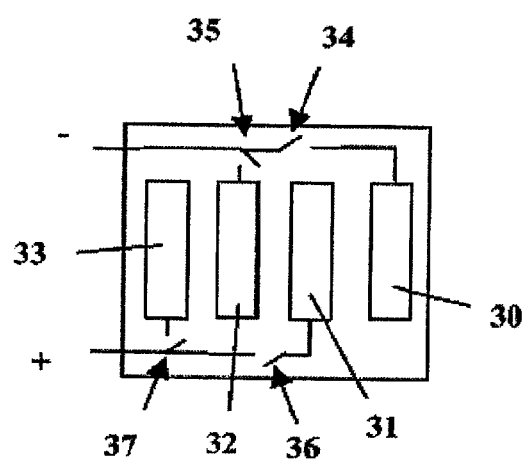
FIGS. 7A and 7B show other embodiments of the invention.
Figure 7B:
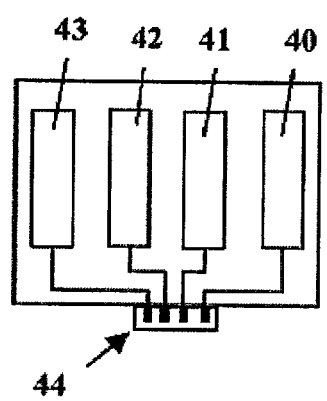

FIGS. 7A and 7B schematically show other particular embodiments of the invention. In the embodiment of FIG. 7A, each active zone 30-33 is connected to a source (for example a stimulator, not represented) through switches 34-37 allowing the connection of any combination of active zones or pairs of active zones to a source by actuation of the switches.

In the embodiment of FIG. 7B, each active zone 40-43 is independently connected to a source (for example a stimulator, not represented) allowing also an independent activation of each single active zone 40-43. In this embodiment, one has also represented a tab 44 that could be used for connection of the set of electrodes to a stimulator, for example, either directly or via a cable or even via a wireless system. The selection of the active zones being activated can then be made at the stimulator level, for example, by specific stimulation programs.

The configuration illustrated in FIG. 7B is interesting in that it allows the activation of each active zone independently. This is useful when one wants to apply a TENS stimulation or an EMS stimulation with the same electrode set.

For example, for a TENS stimulation, active zones 40 and 42 can form negative poles and zones 41 and 43 form positive poles in accordance with the principle of the present invention. For an EMS stimulation, zones 40 and 41 would form a negative pole and zones 42 and 43 and positive pole thereby forming active zones with a larger surface.

Of course, it is possible to invert the poles with respect to the description given above for FIG. 7B, the aim being of having either a succession of alternating poles (for TENS stimulation) or two poles each made of a group of neighboring active zones.

This could also be realized with the configuration of FIG. 7A if all active zones were connected via switches (such as switches 34-37) to the lines "+" and "−".

Of course, the embodiments of FIGS. 7A and 7B are only for illustrative purposes and the configurations are not limited to four active zones: more zones may be present, for example 6, 8, 10, 12, etc. Also the principles illustrated in FIGS. 7A and 7B (individual connection of each active zone) may be applied to the other electrode set configurations and stimulators as described in the present specification or covered by the claims.

Figure 8:
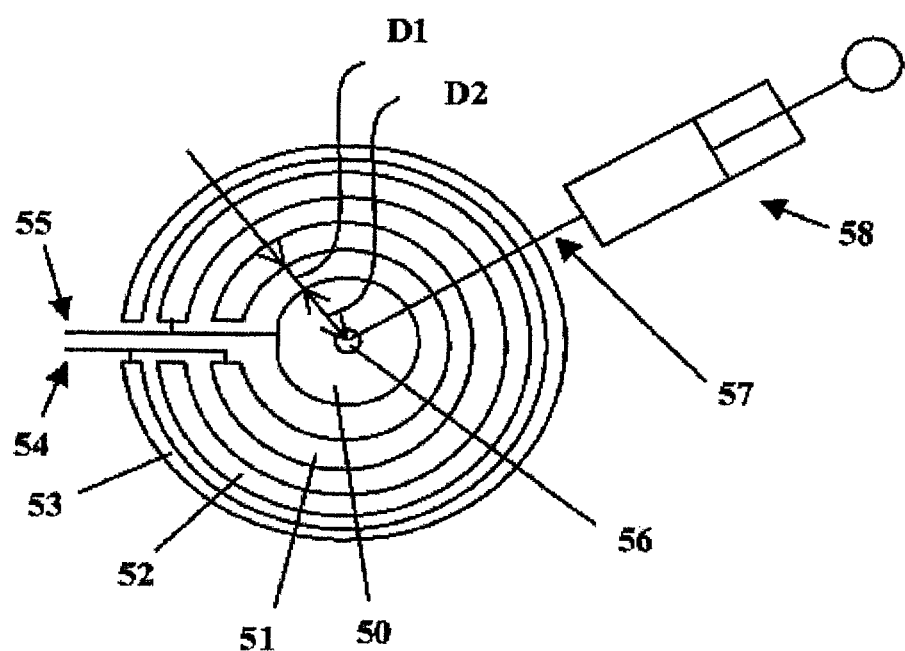
FIG. 8 illustrate a possible use of the electrode set according to the present invention.

In FIG. 8, a particular application of an electrode set of the present invention is illustrated. In this figure, the set is configured with several ring shaped active zones 50-53 (of course other shapes may be envisaged) connected to wires 54, 55. As depicted, zones 50 and 52 are connected to wire 55, and zones 51 and 53 are connected to wire 54. Central zone 50 comprises an opening 56 to allow passage of a needle 57 of a syringe 58. In this embodiment, one may utilize the principle of the invention to create a local anesthesia by maximizing the sensory effect against pain of the device as described in the gate-control theory of pain described in the article of Mark Johnson mentioned above. One can thus take advantage of this local anesthetic effect to, for example, stick the needle 57 of the syringe 58 or a drip (not represented) at this place or even perform surgery. However, as shown, the active zones should be slightly modified in this embodiment to include at least the opening 56 through which the needle or a surgical instrument may pass. Of course, this embodiment may apply to all active zone configurations, in particular to the one illustrated in the present application, as long as it is possible to stick a needle at the desired place (for example by creating an opening). It is of course also possible to avoid this opening and stick the needle (or a surgical instrument) between active zones.

The anesthetic effect may also be useful for superficial skin operations, for example, to remove a pimple or a mole, a melanoma (suspected or real) for a biopsy or for suture. For such applications, one should provide an opening of consequence in at least one of the active zones in application of the principle represented in FIG. 8, or such operations may also be carried out between neighboring active zones. For example, the configuration illustrated in FIG. 6D could be used to this effect, or another configuration illustrated in the present application.

Figure 9A:
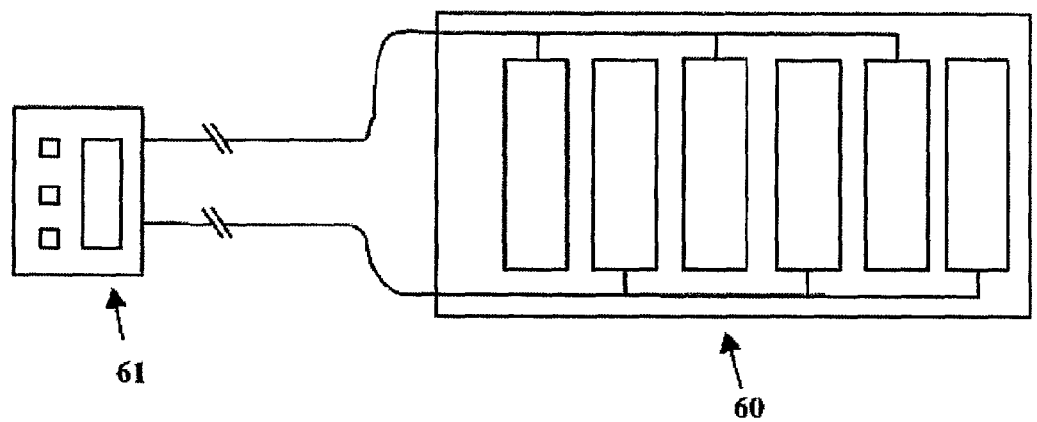
FIGS. 9A and 9B illustrate alternate embodiments of a set according to the present invention with a stimulator.
Figure 9B:
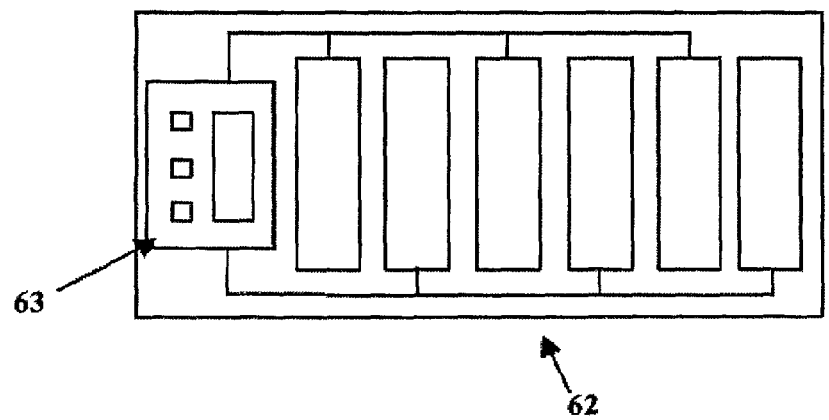
Figure 10A:
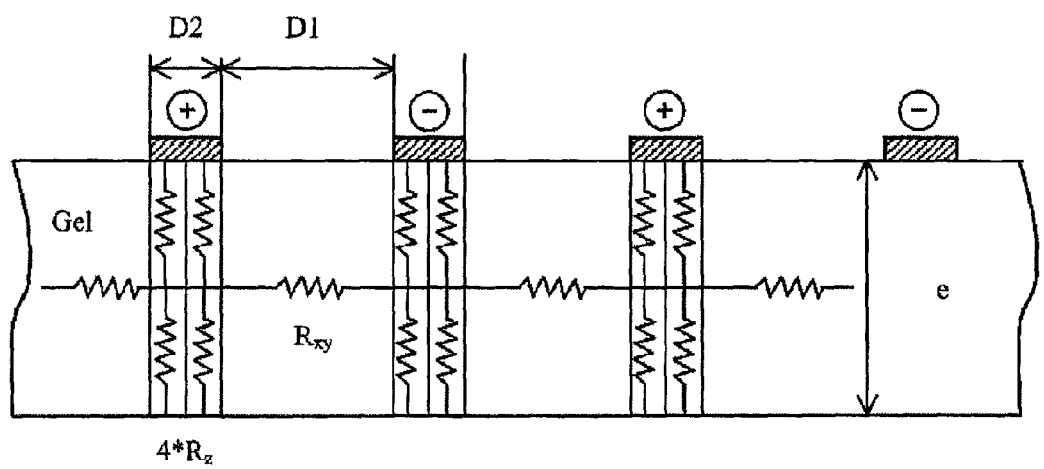
FIG. 10A illustrates a model for dimensioning an electrode set according to one embodiment of the present invention.
Figure 10B:
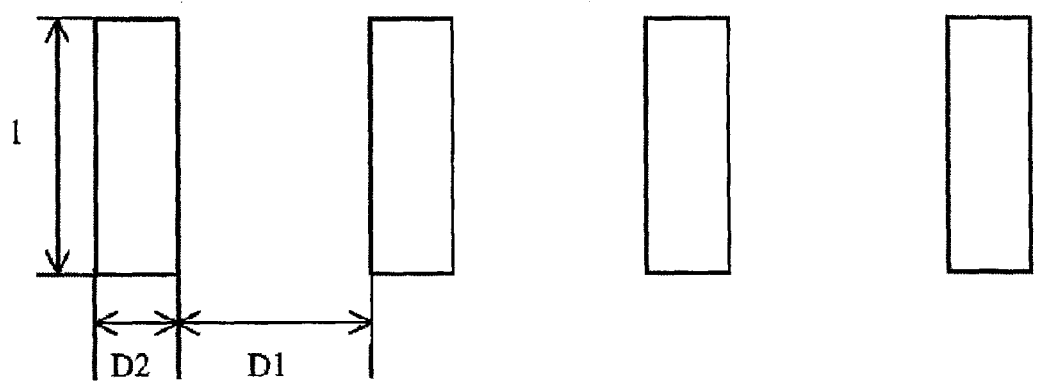
FIG. 10B illustrates a top view of the model shown in FIG. 10A.
Figure 11:
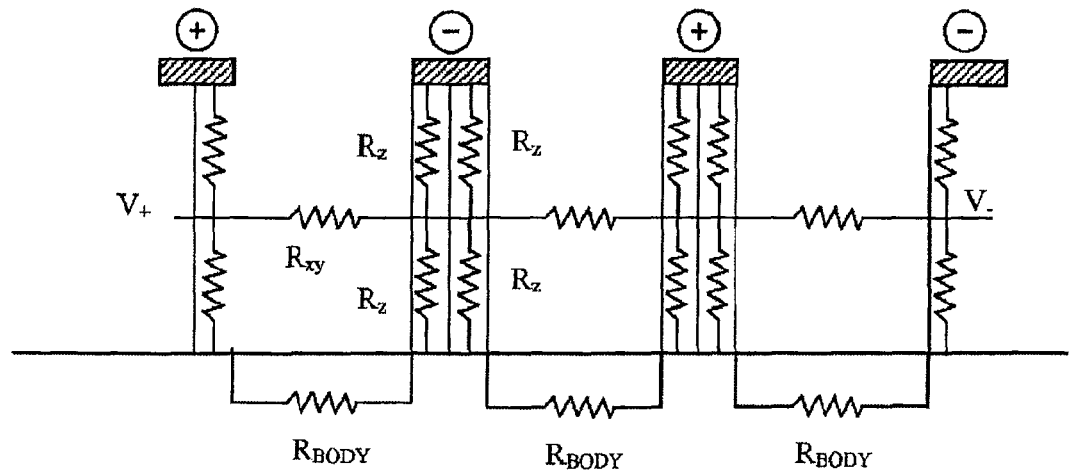
FIG. 11 illustrates a circuit associated with the model.
Figure 12:
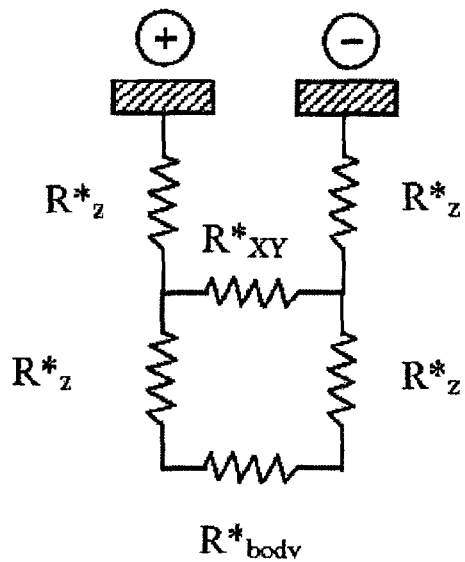
FIG. 12 illustrates a simplified version of the circuit shown in FIG. 11.
Figure 13:
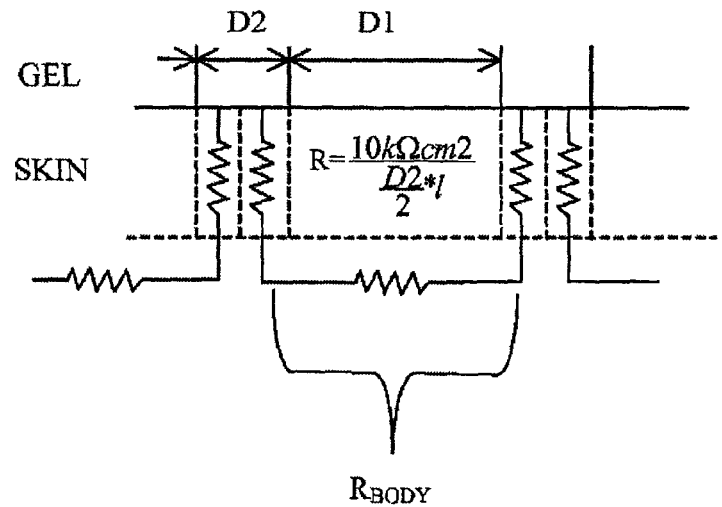
FIG. 13 illustrates a diagram associated with the model.
Figure 14:
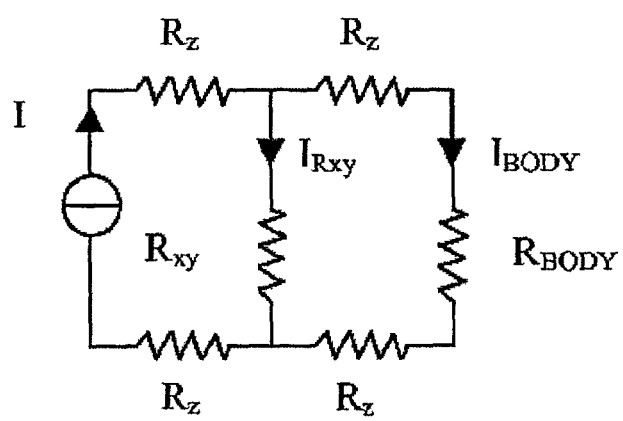
FIG. 14 illustrates an electrical diagram associated with the model.

In a further embodiment, the principle of which may be applied to all embodiments described above, one can integrate at least a part of the circuit of the stimulator on the set of electrodes allowing to connect directly the stimulator on the support. Indeed, in certain configurations and depending on the number of electrodes and sets, the user may end up with a device carrying many wires (at the maximum equal to the number of individual active zones if one chooses the configuration of FIG. 7B) which then will be complicated to connect properly, a problem which creates an error source. By choosing an integrated circuit or a plug-in system for the stimulator, one overcomes this problem of the multiplication of individual wires and can attain a configuration with a reduced number of wires. This alternative is illustrated in FIGS. 9A and 9B with electrode sets 60, 62 and stimulators 61, 63. Of course, the sets 60, 62 represented are only given as a non-limiting examples, and any configuration represented in other drawings of the present application or made according the principles of the present invention may be used as a set of electrodes. In addition, in FIG. 9B, a stimulator 63 can be attached by any suitable means (clipping, Velcro®, etc.) to the set for example, by snap connectors. In this case, it can be advantageous to use the snap connectors as direct contact means for electrical connection of the stimulator to the wire of the set. The use of the device according to the invention is thus made easier and the user needs only to snap stimulator 63 to electrode set 62 without connecting additional wires.

Another aspect of the invention is related to a method for dimensioning the set of the invention. In this method, one uses the electrode set as defined above with a gel layer between the set and the skin of the user and the principles of the dimensioning method are disclosed below with reference to FIGS. 10A-15. A typical example of such an electrode set is the one represented in FIGS. 2 and 3B.

FIGS. 10-15 illustrate the hypothesis and models considered in this dimensioning method. The idea is to maximize the resistivity of the gel in the direction X, Y (Rxy) in order to force the current to penetrate into the body of the user, rather than go through the gel directly from one electrode to a neighboring electrode.

The values of resistivity in both directions are defined as follows (with reference to FIGS. 10A and 10B):

$$Rxy = \rho_{GEL} * \frac{D_1}{e*l},$$

where $\rho_{GEL}$ is the specific resistivity of the gel $$Rz = \rho_{GEL} * \frac{e}{D_2 * l}$$

The resistivity of the body is defined as follows:

$$R_{BODY} \cong 2 * \frac{R_{SPEC}}{\frac{D_2 * l}{2}}$$

$R_{SPEC} \cong 10$ k$\Omega$cm$^2$ is the specific resistivity measured from the surface of the skin at the considered frequencies of stimulation. Of course, this value may change according to the circumstances.

Considering the electrical diagrams of FIGS. 11-14, one can define the following equation for the currents:

$$\frac{I_{body}}{I} = \frac{I_{body}}{I_{body} + I_{Rxy}} = \frac{1}{1 + \frac{I_{Rxy}}{I_{body}}}$$

Accordingly, what is sought is to minimize the ratio $I_{Rxy}/I_{body}$.

It has been found that:
if this ratio is equal to 1, then $$\frac{I_{body}}{I} = 50\%,$$

meaning that 50% of the current is lost in the gel;
if this ratio is equal to 9, then $$\frac{I_{body}}{I} = 10\%,$$

meaning that 90% of the current is lost in the gel;
We have then the following equation:

$$\frac{I_{Rxy}}{I_{body}} = \frac{2Rz + R_{body}}{R_{XY}} = 2*\frac{R_Z}{R_{XY}} + \frac{R_{body}}{R_{XY}} = 2*\frac{e^2}{D_1 D_2} + \frac{4*R_{SPEC}*e}{\rho_{GEL} D_1 D_2} \quad (1)$$

In some embodiments, $\rho_{GEL} \approx 10\text{-}100\Omega$.

As one can see, this equation has two members, one purely geometrical (e, $D_1$ and $D_2$) and a second member which is linked to the resistivity (body and gel).

To sum up, one wishes to optimize three parameters (see FIG. 15):
1) low loss in the electrode set, this parameter being optimized by the equation (1) above
2) no motor stimulation of muscle, this aspect has been discussed above, where it has been shown experimentally that the lateral size of the active zones $D_2$ and the distance $D_1$ between two neighboring active zones were important to optimize the threshold ratio between the TENS effect and the MOTOR effect. In particular, one has demonstrated that $D_1$ and $D_2$ have to be a minimum in order to maximize this threshold ratio.
3) no "no sensitive", meaning the absence of any TENS effect because the current does not go deep enough in the skin or remains in the gel layer without penetration of the skin. For this third parameter, it has been shown that active zones which are too small and too close to one another have this effect, in particular observed when $D_1=1$ mm and $D_2=1$ mm. One can assume that smaller size values will further increase this effect.

Figure 15:
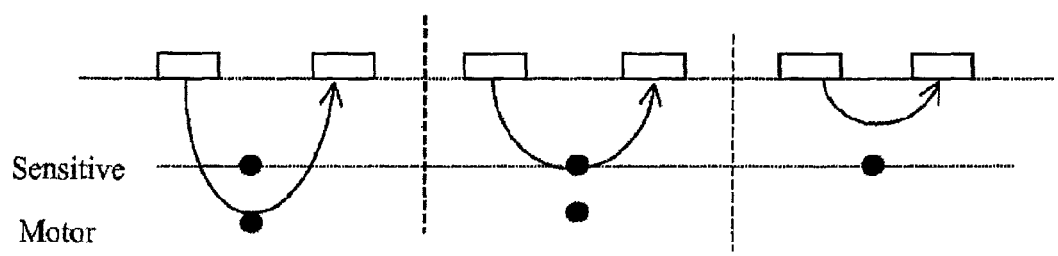
FIG. 15 illustrates three possibilities of stimulation associated with the model.

FIG. 15 represents visually three possibilities of stimulation. Considering the drawings from the left to right, the first one shows a situation in which the current goes too deeply in the skin and stimulates the sensitive nerves and also the muscle nerves, the second drawing shows the optimal situation in which only the sensory nerves are stimulated and the third drawing shows another undesired situation where no nerves are stimulated at all.

From the above, one will understand that if the electrode set is used without a gel layer entirely covering the side of the set that is in contact with the skin of the user for example with gel strips, the experiments and values disclosed in the above mentioned Tables give a basis of optimum sizes for the active zones and their relative position, whereas if a continuous gel layer is placed on side of the set in contact with the skin of the user, it is necessary to further consider the equation (1) indicated above to optimize the values and take this layer into account.

Of course, all values mentioned above are indicative and may be varied according to the circumstances to dimension an electrode set according to the present invention. The present invention thus also provides a method for dimensioning an electrode set using the equation and parameters set above, and also to an electrode set obtained by said method.

As can be readily understood from the above description, the present invention also concerns a method of treatment using the defined electrode set and a method of use of such electrode set. More precisely, the device according to the invention is used for a TENS treatment of the human body for example for pain relief.

Such methods include at least the steps of applying the set of electrodes to the body of a user and activating the zones with a given signal in order to obtain the desired TENS stimulation. In another application, the electrode set can be used for anesthesia as described above.

In these methods, at least the following steps are carried out:
applying an electrode set with active zones to a user;
connecting the stimulator to the set;
applying electrical signals to the user through the active zones.

As can be readily understood from the present specification, the application of the electrode set is made on the treatment location (for example directly on the painful area or where the surgical operation is taking place). Accordingly, the shape and the size of the set and/or of the backing (if present) can be tailored to the shape of the body to optimize the application. Typical examples include, leg, arm, knee, elbow etc.

Then the set of electrode is connected to the stimulator. This can be made by a direct connection of the stimulator to the set or by wires. As will be understood from a skilled reader, the connection to the stimulator may be carried out before the electrode set is applied to the user.

Then, the desired signals are applied by the stimulator to the electrode set.

The signals may be predetermined and memorized in the stimulator (for example predetermined stimulation programs) or they may be chosen by the user and adapted during use.

The stimulator may be connected to the electrode set once the set has been applied to the user, or it may be connected beforehand and then the stimulator is applied to the user.

Typical TENS examples of signal values (amplitude, frequencies waveforms etc) can be taken from the publication "Transcutaneous Electrical Nerve Stimulation (TENS)" of Mark Johnson referenced above in the present specification.

As can be understood, the embodiments described above are given by way of non-limiting examples and equivalent variations are possible, for example on the shapes of the electrodes and their number which are not limited to the one represented in the figures. The wires used as contacting means may be connected in any suitable fashion, by glueing or other connection means mechanical or not (connectors, snaps etc.) Of course, the spacing $D_1$ and the size $D_2$ may not be constant in a set: one may combine different configurations in the same electrode set and use different values for $D_1$ and $D_2$.

In addition, the values $D_1$ and $D_2$ indicated above can similarly be applied on the other shapes of electrodes as mentioned above and as illustrated in the drawings.

It is understood that the embodiments discussed and represented in the drawings are for illustrative purposes and should not be interpreted in a limiting way. In addition, the principles exposed above apply to all the configurations represented. For example the principle of the embodiment of FIG. 5 could be applied to active zones with different shapes as illustrated in other figures of the present application.

In addition, the shape and/or configuration of the electrode said may also be chosen depending on the part of the user's body being stimulated (arm, torso, leg, foot, knee, elbow etc) so many different shape, sizes and number of active zones may be envisaged within the scope of the present invention. Also, as mentioned above, the size D1 and spacings D2 may be maintained constant in a given set or may be varied in the said set. This choice may depend on the desired position of the set on the body and/or the type of treatment envisaged.

From the above, it will be readily understood that many different configurations might be envisaged and are covered by the present application. For the active zones, many equivalent suitable conductive materials (in addition to carbon) may be envisaged.

In addition to the embodiments described above, it is also possible, as an illustrative example, to form an electrode set with only a part of the active zones having the dimensions and distances described in the present specification. For example, some active zones could have a larger lateral size (i.e. $D_2$ over 40 mm) and in between such active zones, a set according the present invention could be placed.

In a further embodiment, using the grouping of active zones described above, it can be envisaged to form a set with active zone having a lateral size of less than 1 mm and also a distance than less than 1 mm between such neighboring active zones, and by grouping such active zones, one obtains an overall active zone lateral size between approximately 1 mm to 40 mm and a spacing also between approximately 1 mm to 40 mm.

The invention claimed is:

1. An electrode set for a stimulation device, the electrode set comprising:
    a plurality of neighboring electrically active zones forming a succession of poles of alternating polarity or being grouped to form groups of poles of alternating polarity and configured to provide current to a body which reaches and stimulates sensory fibers and which does not reach and stimulate muscle fibers, the active zones defined by two combs, each comb comprising a base and parallel teeth connected to the base, wherein the teeth of the combs are intermingled;
    an insulating layer that covers the base of the combs;
    wherein at least one of the plurality of active zones has a lateral size of 1 mm to 40 mm;
    wherein a spacing between neighboring active zones is 1 mm to 40 mm; and
    wherein the electrode set further comprises contacting means connected to the plurality of active zones.

2. The electrode set as defined in claim 1, wherein said lateral size and said spacing are approximately 5.5 mm.

3. The electrode set as defined in claim 1, wherein said lateral size and said spacing are approximately 3 mm.

4. The electrode set as defined in claim 1, wherein said plurality of zones comprises a conductive layer of carbon.

5. The electrode set as defined in claim 1, wherein a conductive layer of carbon is cut to form said active zones.

6. The electrode set as defined in claim 4, wherein said plurality of active zones further comprises a layer of conductive ink.

7. The electrode set as defined in claim 1, further comprising a non-conductive backing layer.

8. The electrode set as defined in claim 1, further comprising a gel layer.

9. The electrode set as defined in claim 1, wherein a gel layer is present on each of the teeth.

10. The electrode set as defined in claim 1, wherein the plurality of active zones comprises:
    a first conductive layer;
    a middle conductive mask placed on said first conductive layer with cut openings, the middle mask having an insulating backing in contact with the first conductive layer; and
    a non-conductive top mask with cut openings allowing access to said first conductive layer and said middle layer.

11. The electrode set as defined in claim 1, wherein the plurality of active zones has a rectangular shape, a circular shape, or a triangular shape.

12. The electrode set as defined in claim 10, wherein the openings have a rectangular shape, a circular shape, or a triangular shape.

13. The electrode set as defined in claim 8, wherein the gel has the shape of gel patches or strips placed on each active zone.

14. The electrode set as defined in claim 1, wherein said contacting means comprise wires connected to said active zones.

15. The electrode set as defined in claim 14, wherein the wires are glued to the active zones.

16. The electrode set as defined in claim 1, wherein the electrode set has an overall longitudinal dimension of about 130 mm and an overall lateral dimension of about 60 mm.

17. An electrode set according to claim 1 further comprising a stimulator connected to said set through said contacting means.

18. The electrode set of claim 1, wherein in the insulating layer comprises a screen.

19. A treatment method comprising:
    applying an electrode set to a part of a user's body, the electrode set comprising
        a plurality of neighboring electrically active zones forming a succession of poles of alternating polarity or being grouped to form groups of poles of alternating polarity, the active zones defined by two combs, each comb comprising a base and parallel teeth connected to the base, wherein the teeth of the combs are intermingled;
        an insulating layer that covers the base of the combs;
        wherein at least one of the plurality of active zones has a lateral size of 1 mm to 40 mm; and
        wherein a spacing between neighboring active zones is 1 mm to 40 mm; and
    applying a stimulation signal to the plurality of active zones so as to provide current to the body which reaches and stimulates sensory fibers and which does not reach and stimulate muscle fibers, wherein each active zone of the plurality of active zones is stimulated with a signal of a selected polarity.

20. The treatment method as defined in claim 19, wherein the treatment is a TENS stimulation.

21. The treatment method according to claim 19, wherein the selected polarity is the same as the polarity of the signals applied to neighboring active zones.

22. A treatment method according to claim 19, wherein the selected polarity is opposite the polarity of the signals applied to neighboring active zones.

23. An electrode set comprising:
a plurality of neighboring electrically active zones forming a succession of poles of alternating polarity or being grouped to form groups of poles of alternating polarity and configured to provide current to a body which reaches and stimulates sensory fibers and which does not reach and stimulate muscle fibers, the active zones defined by two combs, each comb comprising a base and parallel teeth connected to the base wherein the teeth of the combs are intermingled;
an insulating layer that covers the base of the combs;
wherein at least one of the plurality of active zones has a lateral size of 1 mm to 40 mm,
wherein a spacing between neighboring active zones is 1 mm to 40 mm, and
wherein the electrode set further comprises contacting means connected to the plurality of said zones, the plurality of active zones being adapted to interface with an external surface of a patient's body to deliver TENS stimulation.

24. An electrode set comprising:
a plurality of neighboring electrically active zones forming a succession of poles of alternating polarity or being grouped to form groups of poles of alternating polarity and configured to provide current to a body which reaches and stimulates sensory fibers and which does not reach and stimulate muscle fibers, the active zones defined by two combs, each comb comprising a base and parallel teeth connected to the base, wherein the teeth of the combs are intermingled;
an insulating layer that covers the base of the combs;
wherein at least one of the plurality of active zones has a lateral size of 1 mm to 40 mm,
wherein a spacing between neighboring active zones is 1 mm to 40 mm, and
wherein the electrode set further comprises contacting means connected to the plurality of active zones, the plurality of active zones being adapted to interface with an external surface of a patient's body to deliver EMS stimulation.

* * * * *